(12) United States Patent
Satake

(10) Patent No.: US 8,330,808 B2
(45) Date of Patent: Dec. 11, 2012

(54) OPHTHALMIC PHOTOGRAPHING APPARATUS

(75) Inventor: Norimasa Satake, Nukata-gun (JP)

(73) Assignee: Nidek Co., Ltd., Gamagori-Shi (JP)

( * ) Notice: Subject to any disclaimer, the term of this patent is extended or adjusted under 35 U.S.C. 154(b) by 631 days.

(21) Appl. No.: 12/591,044

(22) Filed: Nov. 5, 2009

(65) Prior Publication Data

US 2010/0110171 A1  May 6, 2010

(30) Foreign Application Priority Data

Nov. 5, 2008 (JP) ................................ 2008-283871

(51) Int. Cl.
*H04N 7/18* (2006.01)
*G06F 15/16* (2006.01)

(52) U.S. Cl. ........................................................ 348/78

(58) Field of Classification Search ............... 348/77–78
See application file for complete search history.

(56) References Cited

U.S. PATENT DOCUMENTS

| | | | | |
|---|---|---|---|---|
| 5,905,562 | A * | 5/1999 | Isogai et al. | 351/208 |
| 6,217,172 | B1 * | 4/2001 | Shibutani et al. | 351/204 |
| 7,123,751 | B1 * | 10/2006 | Fujieda | 382/115 |
| 7,510,282 | B2 * | 3/2009 | Ueno et al. | 351/206 |
| 7,824,035 | B2 * | 11/2010 | Yamada et al. | 351/206 |
| 2003/0103212 | A1 | 6/2003 | Westphal et al. | |
| 2005/0117116 | A1 * | 6/2005 | Murakami | 351/211 |
| 2011/0170062 | A1 * | 7/2011 | Isogai et al. | 351/206 |

FOREIGN PATENT DOCUMENTS

| | | |
|---|---|---|
| JP | A-2008-29467 | 2/2008 |
| WO | WO 2006/105903 A2 | 10/2006 |
| WO | WO 2008/052793 A1 | 5/2008 |

OTHER PUBLICATIONS

Ferguson et al., "Tracking optical coherence tomography," *Optics Letter*, Optical Society of America, Washington, DC, vol. 29, No. 18, Sep. 15, 2004, pp. 2139-2141.
Feb. 13, 2012 Office Action issued in European Patent Application No. 09 175 157.8.
European Search Report issued in European Patent Application No. 09 17 5157 on Mar. 22, 2010.
Stevenson et al., "Correcting for Miniature Eye Movements in High Resolution Scanning Laser Ophthalmoscopy," Progress in Biomedical Optics and Imaging—Proceedings of SPIE, 2005, pp. 145-151, vol. 5688.
Velthoven et al., "Recent Developments in Optical Coherence Tomography for Imaging the Retina," Progress in Retinal and Eye Research, 2007, pp. 57-77, vol. 26, No. 1.

* cited by examiner

*Primary Examiner* — Zarni Maung
(74) *Attorney, Agent, or Firm* — Oliff & Berridge, PLC

(57) ABSTRACT

An ophthalmic photographing apparatus having a photographing unit having a projection optical system having a light source and a scanner changing a reflection direction of light and scanning an eye portion in X,Y-directions with measurement light, and an optical system having photodetectors and making the reflected light enter the photodetectors, a unit controlling the photographing unit to scan the given portion plural times in a scanning region and obtain image information pieces based on a photodetector signal, and a unit dividing the region in the X,Y-directions of each information into regions and obtain information on deviation between the image information pieces for each divided region, obtain image information for each divided region, in which deviation has been corrected, with reference to one of the image information pieces based on the deviation information, add and average the image information pieces for each corresponding divided region to obtain image information.

10 Claims, 6 Drawing Sheets

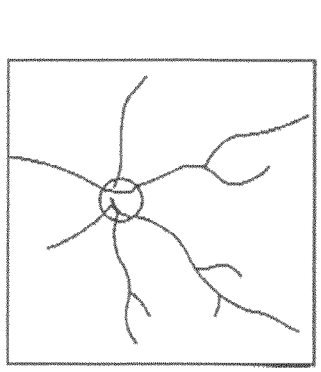
FIG. 9A
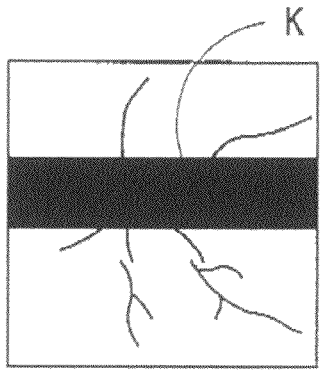
FIG. 9B
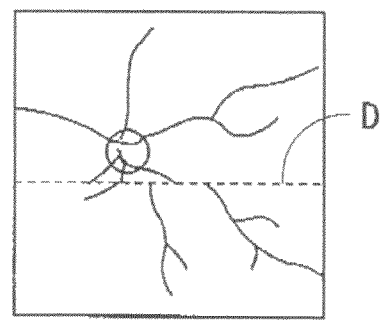
FIG. 9C
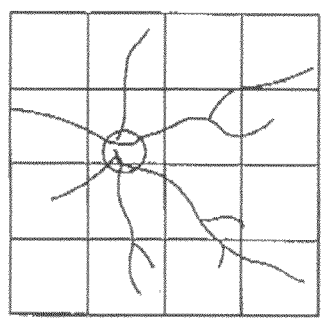
FIG. 10A
All: ××pixel
A: ××pixel
B: ××pixel
C: ××pixel
FIG. 10B

OPHTHALMIC PHOTOGRAPHING APPARATUS

BACKGROUND OF THE INVENTION

1. Field of the Invention

The present invention relates to an ophthalmic photographing apparatus arranged to obtain a tomographic image or a front image of a given portion of an examinee's eye.

2. Description of Related Art

Conventionally, as an apparatus having a light scanning system and arranged to obtain a tomographic image or a front image of an examinee's eye, there is known an ophthalmic OCT (Optical Coherence Tomography) apparatus based on the principle of an optical coherence tomograph (see Japanese Patent Application Unexamined Publication No. 2008-29467) or a light scanning optometry apparatus based on the principle of a confocal optical system (an ophthalmic SLO (Scanning Laser Opthalmoscope). In this kind of apparatus, various noises could occur in the obtained image.

In general, if a noise occurs in an obtained image, a plurality of images obtained in one region are added, and pixel values are added and averaged. If a positional deviation occurs between the obtained images, the positional deviation between the obtained images is detected by comparing characteristic points of the obtained images and is corrected by moving on an image basis.

In the apparatus arranged to obtain the tomographic image or the front image of the eye by using the light scanning system as described above, fine movement of, the eye during scanning with measurement light due to involuntary eye movement or other reasons may generate a positional deviation in one obtained image. However, the above-described image addition method cannot deal with a local, fine positional deviation caused during the scanning with the measurement light. The addition without properly correcting the local positional deviation generally results in that a favorable image that is intended cannot be obtained.

SUMMARY OF THE INVENTION

An object of the invention is to overcome the problems described above and to provide an ophthalmic photographing apparatus capable of obtaining a favorable tomographic image or a favorable front image of an examinee's eye.

To achieve the objects and in accordance with the purpose of the present invention, an ophthalmic photographing apparatus arranged to obtain an image of an examinee's eye has a photographing unit having a projection optical system having a light source and a scanner arranged to change a reflection direction of light, and arranged to scan a given portion of the eye in X- and Y-directions with at least a part of the light omitted from the light source defining measurement light, and a photo-receiving optical system having one or more photodetectors and arranged to make the measurement light reflected from the given portion of the eye enter the one or more photodetectors, a photographing control unit arranged to control operation of the photographing unit to scan the given portion a plurality of times in a given scanning region and obtain a plurality of pieces of image information based on a signal from the one or more photodetectors, and an image information processing unit arranged to (a) divide the scanning region in the X- and Y-directions of each of the plurality of pieces of image information into a plurality of regions and obtain information on a positional deviation between the plurality of pieces of image information for each of the divided regions, (b) obtain image information for each of the divided regions, in each of which the positional deviation has been corrected, with reference to one of the plurality of pieces of image information based on the obtained positional deviation information, and (c) add and average the plurality of pieces of image information for each of their corresponding divided regions to obtain one piece of image information.

In another aspect of the present invention, an ophthalmic photographing apparatus arranged to obtain an image of an examinee's eye has a photographing unit having an interference optical system having a light source and arranged to divide light emitted from the light source into measurement light and reference light, guide the reference light to a reference optical system, guide the measurement light to a projection optical system arranged to scan a given portion of the eye in X- and Y-directions with the measurement light by using a scanner, and combine the measurement light reflected from the given portion and the reference light into interference light by using a light combining member, and arranged to make the interference light enter one or more photodetectors, a photographing control unit arranged to control operation of the photographing unit, scan a plurality of times the given portion in a given scanning region, and obtain a plurality of pieces of image information by obtaining a signal from the one or more photodetectors, and an image information processing unit arranged to (a) divide the scanning region in the X- and Y-directions of each of the pieces of image information into a plurality of regions and obtain information on a positional deviation between the pieces of image information for each of the divided regions, (b) obtain image information for each of the divided regions, in each of which the positional deviation has been corrected, with reference to one of the plurality of piece of image information based on the obtained positional deviation information, and (c) add and average the plurality of pieces of image information for each of their corresponding divided regions to obtain one piece of image information.

Additional objects and advantages of the invention are set forth in the description which follows, are obvious from the description, or may be learned by practicing the invention. The objects and advantages of the invention may be realized and attained by the ophthalmic photographing apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIGS. 9A to 9C are views showing examples of the OCT fundus image obtained by the three-dimensional image obtainment; and FIG. 10A is a view showing image division when detecting a local positional deviation amount between the SLO fundus image and the OCT fundus image, and FIG. 10B is a view showing an example of displaying a result of the detection of the positional deviation amount on the monitor.

DETAILED DESCRIPTION OF THE PREFERRED EMBODIMENTS

Figure 1:
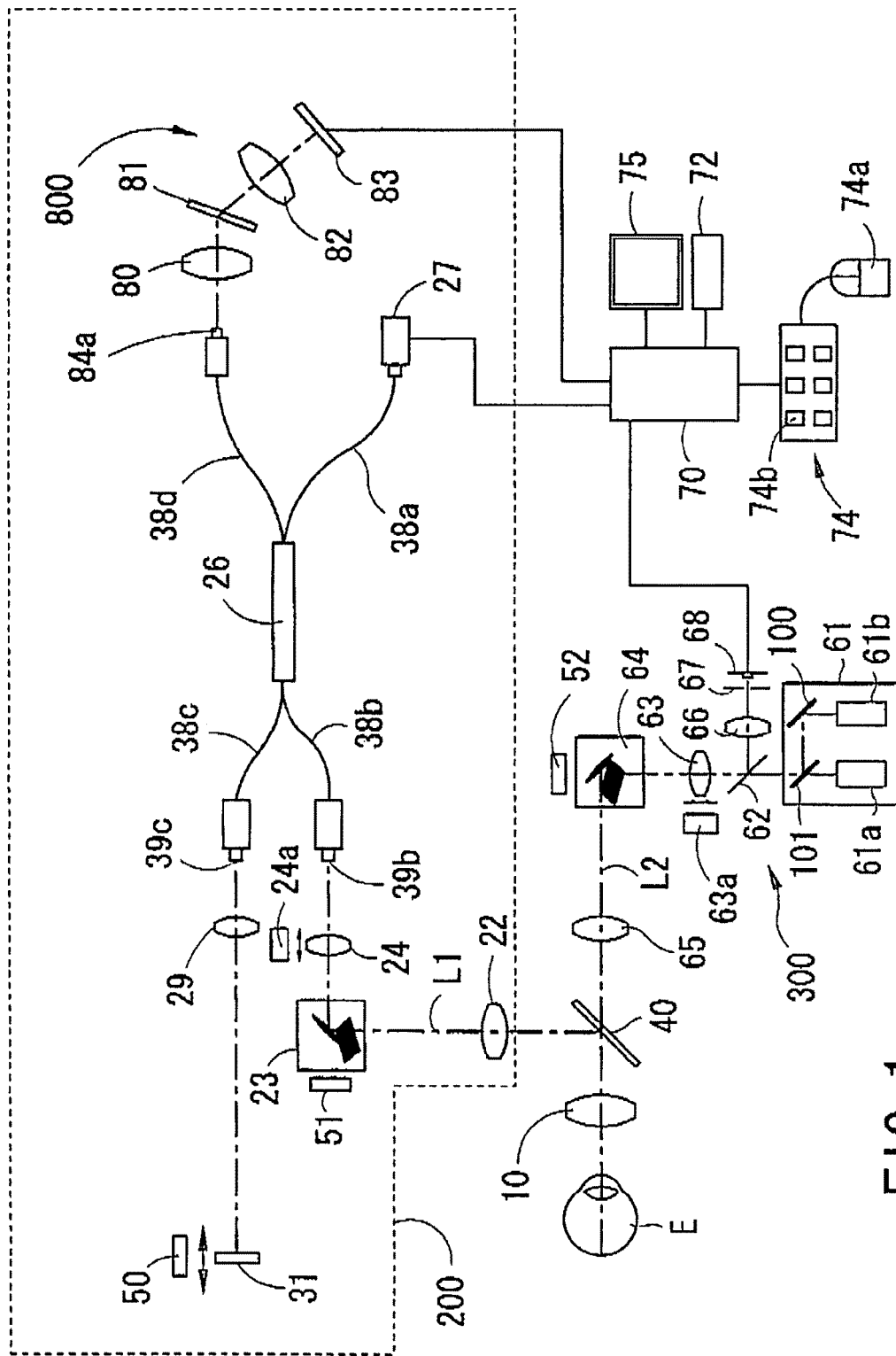
FIG. 1 is a view showing an optical system and a control system of an ophthalmic photographing apparatus according to a preferred embodiment of the present invention.

A detailed description of one preferred embodiment of an ophthalmic photographing apparatus embodied by the present invention is provided below with reference to the accompanying drawings. FIG. 1 is a view showing an optical system and a control system of the ophthalmic photographing apparatus according to the present preferred embodiment of the present invention. In the present preferred embodiment of the present invention, a depth direction of an examince's eye E is referred to as a Z-direction (a direction of an optical axis L1), a horizontal direction is referred to as an X-direction, and a vertical direction is referred to as a Y-direction.

Referring to FIG. 1, the optical system is roughly divided into an interference optical system, 200 arranged to obtain a tomographic image of a fundus of the eye E by an interferometric technique in a non-invasive method (hereinafter, referred to as the OCT optical system 200), and a scanning laser opthalmoscope optical system 300 arranged to obtain an SLO fundus image for observation by illuminating the fundus with infrared light (hereinafter, referred to as the SLO optical system 300). A Fourier-domain OCT optical system is used as the OCT optical system 200.

A dichroic mirror 40 defines a light-dividing member, and has a property of reflecting measurement light which is emitted from a measurement light source 27 of the OCT optical system 200 (e.g., light with wavelengths in the vicinity of 840 nm), and a property of transmitting laser light which is emitted from a light emitting unit 61 of the SLO optical system 300 (e.g., light different from the light from the OCT light source 27 and with wavelengths in the vicinity of 780 nm). In this case, the dichroic mirror 40 makes the optical axis L1 of the OCT optical system 200 coaxial with an optical axis L2 of the SLO optical system 300.

First, a description of the OCT optical system 200 which is disposed at a reflection side of the dichroic mirror 40 is provided. The OCT light source 27 is arranged to emit low coherent light to be used as measurement light and reference light of the OCT optical system 200. An SLD light source is preferably used as the OCT light source 27. Specifically, a light source having a center wavelength of 840 nm and a bandwidth of 50 nm is used, for example. A fiber coupler 26 functions as both of a light dividing member and a light combining member. The light from the OCT light source 27 passes through an optical fiber 38a that functions as a light guide, and is divided into the reference light and the measurement light by the fiber coupler 26. The measurement light passes through an optical fiber 38b and heads for the eye E. The reference light passes through an optical fiber 33c and heads for a reference mirror 31.

On an optical path where the measurement light travels to the eye E, an end portion 39b of the optical fiber 38b from which the measurement light exits, a focusing lens 24 which is movable in an optical axis direction in accordance with refractive error of the eye E, a scanning unit 23 which is defined by a combination of two galvano mirrors capable of scanning the fundus in the X- and Y-directions with the measurement light by driving of a scanning driving mechanism 51, and a relay lens 22 are disposed. In the scanning unit 23 according to the present preferred embodiment of the present invention, scanning directions of the scanning of the fundus with the measurement light can be arbitrarily set by arbitrarily adjusting reflection angles of the measurement light by using the two galvano mirrors. Thus, a tomographic image of a given portion of the fundus can be obtained. The end portion 39b of the optical fiber 38b is disposed so as to be conjugate with the fundus, and the two galvano mirrors of the scanning unit 23 are disposed at positions substantially conjugate with a pupil of the eye E.

The measurement light reflected from the fundus passes through the objective lens 10, is reflected by the dichroic mirror 40, and heads for the OCT optical system 200, where the measurement light enters the end portion 39b of the optical fiber 38b via the relay lens 22, the two galvano mirrors of the scanning unit 23, and the focusing lens 24. The measurement light which enters the end portion 39b reaches an end portion 84a of an optical fiber 38d via the optical fiber 38b, the fiber coupler 26, and the optical fiber 38d.

On an optical path where the reference light travels to the reference mirror 31, an end portion 39c of the optical fiber 38c from which the reference light exits, a collimator lens 29, and the reference mirror 31 are disposed. The reference mirror 31 is movable in an optical axis direction by a reference-mirror driving unit 50 to change the optical path length of the reference light.

The reference light which is thus formed from the light emitted from the OCT light source 27, and the reflection light from the fundus which is formed from the measurement light with which the fundus is illuminated are combined by the fiber coupler 26 to be made into interference light. Then, after passing through the optical fiber 38d, the interference light exits from the end portion 84a. A spectral optical system (a spectrometer unit) 800 arranged to disperse the interference light into frequency components in order to obtain an interference signal for each of the frequencies includes a collimator lens 80, a grating mirror (a diffraction grating) 81, a condenser lens 82, and a photodetector 83. A one-dimensional detector (a line sensor) which has sensitivity to an infrared range is used as the photodetector 83.

To be specific, the interference light exiting from the end portion 84a is made into parallel light by the collimator lens 80, and then is dispersed into the frequency components by the grating mirror 81. The interference light dispersed into the frequency components is collected on a photo-receiving surface (array) of the photodetector 83 via the condenser lens 82. Thus, spectral information on interference fringes is recorded at the photodetector 83. Then, the spectral information is inputted into a control unit 70, and is analyzed by performing the Fourier transform thereon, whereby information in the depth direction of the eye E (an A-scan signal) can be obtained. The control unit 70 can obtain a tomographic image by controlling the scanning unit 23 to scan the fundus in a predetermined traverse direction with the measurement light. For example, the scanning with the measurement light in the X- or Y-direction allows a tomographic image on an X-Z or Y-Z plane of the fundus to be obtained (in the present preferred embodiment of the present invention, a mode of thus obtaining the tomographic image by one-dimensionally scanning the fundus with the measurement light is referred to as B-scan). The obtained tomographic image is stored in a memory 72 connected to the control unit 70. It is also possible to obtain a three-dimensional image of the fundus by two-dimensionally scanning the fundus in the X- and Y-directions with the measurement light. The obtainment of an OCT image in the present preferred embodiment of the present invention is made with the use of the two galvano mirrors of the scanning unit 23.

Next, a description of the SLO optical system (a confocal optical system) 300 which is disposed at a transmission side of the dichroic mirror 40 is provided. The SLO optical system 300 is roughly divided into an illumination optical system arranged to illuminate the fundus with light, and a photo-receiving optical system arranged to photo-receive the illumination light reflected from the fundus with the use of a photodetector. The SLO optical system 300 obtains a front image of the fundus based on a photo-receiving signal outputted from the photodetector.

The emitting unit 61 has a first light source (a SLO light source) 61a arranged to emit light in an infrared wavelength range (e.g., light with a wavelength of 780 nm), a second light source (a fixation light source) 61b arranged to emit light in a visible wavelength range (e.g., light with a wavelength of 630 nm), a mirror 100, and a dichroic mirror 101. As the first light source 61a and the second light source 61b, light sources arranged to emit light with high intensity and high directivity (e.g., laser diode light sources and SLD light sources) are used. The infrared light from the first light source 61a passes through the dichroic mirror 101, exits from the emitting unit 61, and heads for a beam splitter 62. The visible light from the second light source 61b is deflected by the mirror 100, and is reflected by the dichroic mirror 101 to be made coaxial with the infrared light from the first light source 61a. The first light source 61a is used for obtaining a front fundus image for observation, and the second light source 61b is used for guiding a line of sight of the eye E.

On an optical path where the laser light (measurement light or fixation light) from the emitting unit 61 travels to the eye E, a focusing lens 63 which is movable in an optical axis direction in accordance with the refractive error of the eye E, a scanning unit 64 which is defined by a combination of a galvano mirror and a polygon mirror capable of rapidly scanning the fundus in the X- and Y-directions with the measurement light by driving of a scanning driving mechanism 52, a relay lens 65, and the objective lens 10 are disposed. Reflecting surfaces of the galvano mirror and the polygon mirror of the scanning unit 64 are disposed at positions substantially conjugate with the pupil.

The beam splitter 62 is disposed between the emitting unit 61 and the focusing lens 63. At a reflection side of the beam splitter 62, a condenser lens 66, a confocal opening 67 disposed at a position conjugate with the fundus, and a SLO photodetector 68 are disposed to constitute a confocal optical system.

The laser light (the measurement light or the fixation light) from the emitting unit 61 is transmitted through the beam splitter 62, and then reaches the scanning unit 64 via the focusing lens 63, where a reflecting direction of the laser light is changed by driving of the galvano mirror and the polygon mirror. The laser light reflected by the scanning unit 64 is transmitted through the dichroic mirror 40 via the relay lens 65, and is then collected on the fundus via the objective lens 10.

The laser light reflected from the fundus (the measurement light) passes through the objective lens 10, the relay lens 65, the galvano mirror and the polygon mirror of the scanning unit 64, and the focusing lens 63, and is reflected by the beam splitter 62. Then, the laser light is collected by the condenser lens 66, and then is detected by the photodetector 68 via the confocal opening 67. A photo-receiving signal outputted from the photodetector 68 is inputted into the control unit 70, and the control unit 70 obtains a front image of the fundus based on the photo-receiving signal. The obtained front image is stored in the memory 72. The obtainment of an SLO image is made by scanning the fundus in the vertical direction (an auxiliary scanning direction) with the laser light with the use of the galvano mirror of the scanning unit 64, and scanning the laser light in the horizontal direction (a main scanning direction) with the use of the polygon mirror of the scanning unit 64.

The control unit 70 is connected with a display monitor 75 in order to control an image to be displayed thereon. In addition, the control unit 70 is connected with the memory (a storing unit) 72, an operation unit 74 for making various operations, the scanning driving mechanism 51, the scanning driving mechanism 52, the reference-mirror driving unit 50, a first driving mechanism 63a arranged to move the focusing lens 63 in the optical axis direction, a second driving mechanism 29a arranged to move the focusing lens 24 in the optical axis direction, and other members.

The control unit 70 forms a fundus tomographic image by performing image processing based on a photo-receiving signal outputted from the photodetector 83 and a front fundus image by performing image processing based on the photo-receiving signal outputted from the photodetector 68.

The memory 72 stores images obtained in times past, photographing conditions during the image obtainment, and other data. To be specific, data on a past tomographic image and data on a past front image obtained in association with the past tomographic image are stored in correspondence with patient identification information (e.g., ID number, name). In addition, information on a past presenting position of a fixation target (a fixation lamp) and information on a past scanning position with the measurement light are stored as information on an obtainment position of the past tomographic image together with the image data.

The scanning position information specifically includes scanning center coordinates indicating a center position of the measurement light with which the fundus is two-dimensionally scanned and information on a scanning region having a reference position at the scanning center coordinates. The scanning region information includes a scanning pattern with the measurement light (e.g., line, cross, circle) and a scanning region of the scanning pattern. The scanning position information is not limited thereto, and may include information on a display position of scan lines (to be described later) displayed on the monitor 75, information on driving of the scanning unit 23, and other information.

The information on the past presenting position of the fixation target includes coordinates of the past presenting position of the fixation target, a position of driving of the scanning driving mechanism 52 when lighting the light source 61b, and other information.

The memory 72 additionally stores other photographing conditions such as positions of the focusing lenses 24 and 63, a position of the reference mirror 31, gains of the photodetectors 68 and 83, and contrast of the images in association with the patient identification information.

The operation unit 74 operated by an examiner is provided with a mouse 74a defining an operation member for various operations, photographing switches 74b, a key board, and other members. The mouse 74a coordinates with the display on the monitor 75, and is used for setting a current scanning position with the measurement light, setting a current presenting position of the fixation target, and other operations. For the control unit 70, the memory 72, the operation unit 74, and the monitor 75, dedicated members defined by devices may be used, or a personal computer (PC) may be used.

Figure 2:
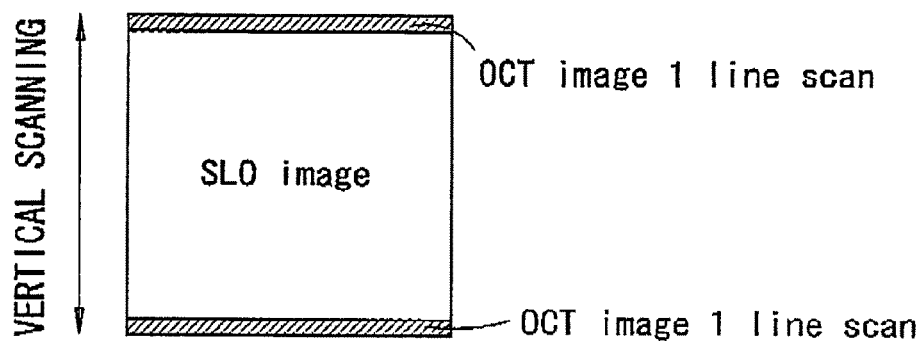
FIG. 2 is a view for explaining an operation of the apparatus when obtaining an OCT image and an SLO image in succession.

Next, a description of a method of obtaining the tomographic image on the X-Z plane by the B-scan (a B-scan image) is provided. FIG. 2 is a view for explaining the operation of the apparatus at the time of obtaining the OCT image and the SLO image in succession. The control unit 70 makes changeover of light with which the fundus is irradiated in order to obtain the image of the fundus between the measurement light from the OCT optical system 200 and the laser light from the SLO optical system 300 by turning on and off the OCT light source 27 and the SLO light source 61a alternately. Accordingly, the interference signals from the photodetector 83 of the OCT optical system 200 and the photo-receiving signals from the photodetector 68 of the SLO optical system 300 are inputted into the control unit 70 in succession (see Japanese Patent Application Unexamined Publication No. 2008-29467).

When obtaining the tomographic image, the control unit 70 controls the light source 61b to be turned on and off in synchronization with the two-dimensional scanning by the driving of the scanning unit 64 in order to guide the line of sight of the eye E. To be specific, the control unit 70 controls the light source 61b to be turned on when a scanning region by the scanning unit 64 reaches a region corresponding to a given fixation position, and controls the light source 61b to be turned off when the scanning region by the scanning unit 64 is out of the corresponding region. Accordingly, the fixation lamp is formed at the given fixation position.

Figure 3:
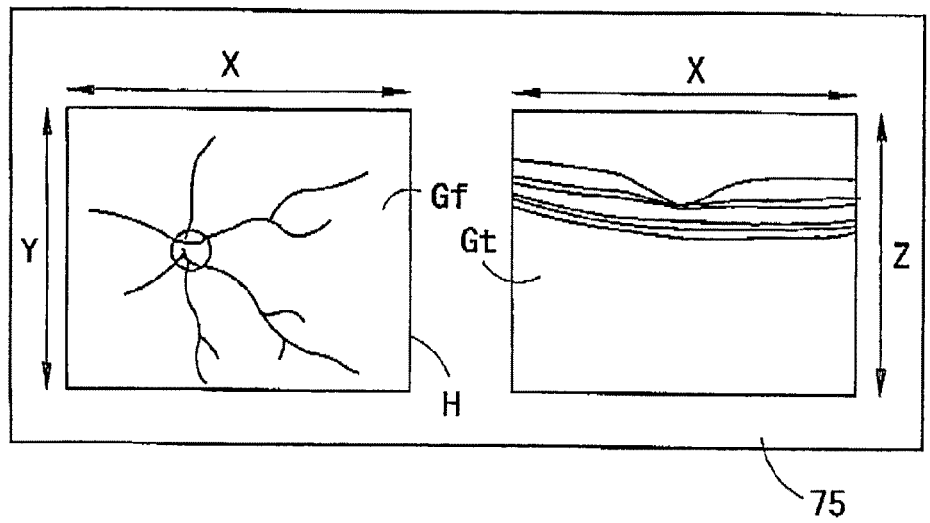
FIG. 3 is a view showing an OCT fundus image and an SLO fundus image displayed in parallel on a monitor.

A description of the operation of the apparatus having the configuration described above is provided. In this operation, the control unit 70 drives and controls the OCT optical system 200 and the SLO optical system 300 to keep obtaining an OCT image and an SLO image for each frame, and controls the monitor 75 to always renew the OCT image Gt and the SLO image Gf displayed thereon (refer to FIG. 3).

First, the examiner instructs the examinee to gaze at the fixation lamp, and performs alignment of the apparatus using a joystick (not shown) such that the measurement optical axis L1 is placed at a pupil center of the eye E while observing an anterior-segment observation image of the eye E which is picked up by an anterior-segment observation camera (not shown) on the monitor 75. When the alignment with respect to the eye E is complete, the front image of the fundus by the SLO optical system 300 (the SLO fundus image) becomes obtainable and the SLO fundus image shows up on the monitor 75.

Follow Up Mode

Figure 4:
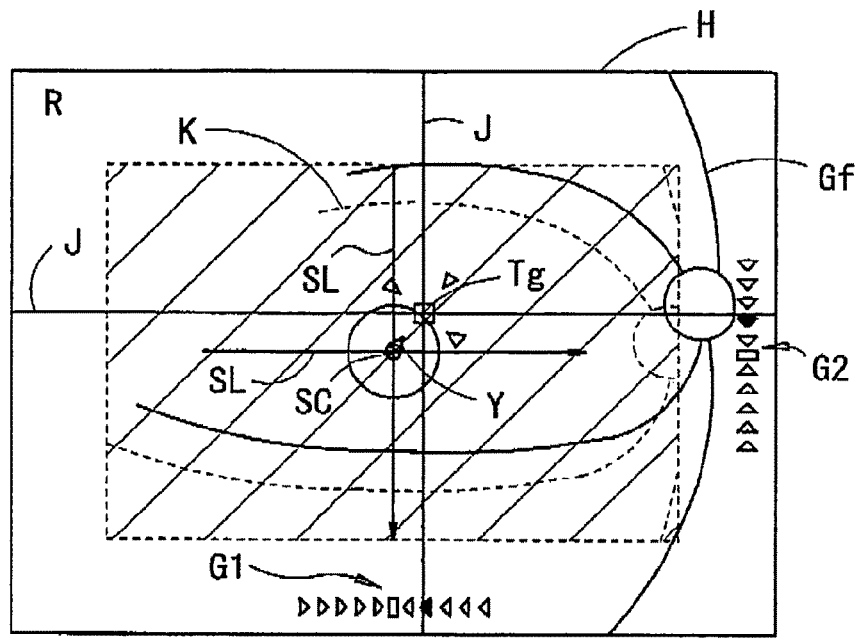
FIG. 4 is a view showing a two-dimensional image (front image) observation screen in a photographing mode for measuring a portion the same as a portion of a tomographic image obtained in times past.

In a display region H of the front image on the monitor 75, an SLO image Gf obtained by the SLO optical system 300 (a current front image) is displayed in real time (see FIG. 4). In the case of testing a revisiting patient for follow-up, for example, when a given switch is operated by the examiner, the control unit 70 retrieves the data on the past front image and the information on the obtainment position of the past tomographic image which have been stored in the memory 72.

The control unit 70 sets the presenting position of the fixation target based on the information on the past presenting position of the fixation target stored in association with the retrieved past front image in the memory 72. Thus, the fixation target is presented at a position the same as that of the past testing, and therefore, the current front image Gf displayed on the monitor 75 becomes almost the same as the past front image. However, the current front image Gf could have a slight difference with respect to the past front image due to a fixation state of the examinee, an alignment state, and other reasons. In addition, the position of the fixation lamp is difficult to reconstruct when using an external fixation lamp. The control unit 70 may reconstruct other photographing conditions (e.g., the position of the focusing lens).

Display of Past Front Image

The control unit 70 performs image processing to cut out an image K in a center region from the data on the past front image stored in the memory 72. The past front image K has such a size that allows for distinguishing the past front image K from the current front image Gf, preventing the past front image K from overlapping with other display items (e.g., an indicator), checking a positional deviation by using an image center portion, and others.

The control unit 70 colors the past front image K to be distinguishable from the current front image Gf and processes the past front image K to be a semi-transparent image with transparency. In addition, reversing on the past front image K makes it easier to distinguish the past front image K from the current front image Gf. The control unit 70 makes a superimposing display of the processed past front image K (see the hatched portion in FIG. 4) on the current front image Gf.

The past front image K is displayed in the display region H such that the image center of the display region H and the image center of the past front image K coincide with each other. Thus, the examiner is allowed to visually observe a positional deviation direction and a positional deviation amount of the current front image Gf from the past front image K obtained substantially simultaneously with the past tomographic image.

Scan Lines SL and Scanning Center Indication SC

The control unit 70 makes a superimposed display of scan lines SL indicating the current scanning position and the scanning pattern on the current front image Gf. In the present preferred embodiment of the present invention, the control unit 70 displays a scanning center indication SC corresponding to the scanning center coordinates at a center position of the scan lines SL.

In addition, the control unit 70 sets a scanning position corresponding to the information on the past scanning position in the memory 72 as an initial scanning position with the measurement light. The initial scanning position is set based on a signal outputted from the memory 72. The control unit 70 displays the scan lines SL at a position corresponding to the initial scanning position. In this case, a display position of the scanning center indication SC corresponds to the scanning center coordinates of the past testing in the display region H. A display position of the scan lines SL corresponds to the scanning region of the past testing in the display region H with reference to the past scanning center coordinates.

When a given adjusting unit (e.g., a mouse) is operated by the examiner after the initial setting described above, the control unit 70 changes the current scanning position with the measurement light based on an operation signal outputted from the adjusting unit and displays the scan lines SL at a display position corresponding to the changed current scanning position. Thus, the display position of the scan lines SL is changed in accordance with the change of the current scanning position. In this case, the scan lines SL is moved on a front image (two-dimensional image) observation screen by drag operation of the mouse, for example.

A correlation between the scanning position with the measurement light by the scanning unit 23 and the display position of the scan lines SL on the display region H is preset. The control unit 70 controls the driving of the two galvano mirrors of the scanning unit 23 appropriately in order to scan the scanning region corresponding to the set display position of the scan lines SL with the measurement light.

Detection of Positional Deviation Between Current Front Image and Past Front Image The control unit 70 first compares the past front image stored in the memory 72 and the current front image Gf and performs image processing to detect (calculate) a positional deviation direction and a positional deviation amount $\Delta d1$ of the current front image Gf from the past front image. The control unit 70 uses the past front image, the base of the past front image K, as a reference image, and calculates the positional deviation direction and the positional deviation amount between the current front image Gf obtained in real time and the reference image. Thus, the information on the positional deviation from the past front image is obtained.

As the method of detecting the positional deviation between the two images as described above, various image processing methods may be used (e.g., a method of using various correlation functions, a method of using the Fourier transform, a method based on matching of characteristic points).

For example, a given reference image (e.g., a past fundus image) or an object image (a current fundus image) is displaced on a pixel basis, and the positional deviation position and the positional deviation amount between the images when the images coincide most favorably (when a correlation between the images becomes highest) are detected. Alternatively, characteristic points common to the given reference image and the object image are extracted, and the positional deviation position and the positional deviation amount between the extracted characteristic points are detected.

A phase only correlation function may be used as a function for obtaining the positional deviation between the two images. In this case, each of the images is subjected to the Fourier transform to obtain the phase and amplitude of frequency components. The obtained amplitude is normalized to the size 1 relative to the frequency components. Then, phase differences between the two images are calculated for, the respective frequencies, and they are subjected to the inverse Fourier transform.

If no positional deviation is detected between the two images, the addition of only cosine waves is performed, and the peak develops at an origin point (0,0). If a positional deviation is detected between the two images, the peak develops at a position corresponding to the positional deviation direction and the positional deviation amount. Accordingly, the positional deviation amount and the positional deviation direction between the two images are obtained by calculating a position of the peak. By this method, the positional deviation between the fundus images can be detected with high accuracy within a short period of time.

Display of Target Mark Tg

When the positional deviation is detected, the control unit 70 retrieves the information on the past scanning position with the measurement light from the memory 72, and corrects the information on the scanning position based on the detected positional deviation direction and the detected positional deviation amount $\Delta d1$. Then, the control unit 70 displays a target mark Tg at a position corresponding to the corrected information on the scanning position (a scanning target position). The target mark Tg is used as a target for adjusting the current scanning position to a portion substantially the same as a portion of the past tomographic image, and is displayed while being superimposed on the current front image Gf.

To be more specific, the target mark Tg is displayed while being offset (corrected) by the positional deviation amount $\Delta d1$ from the past scanning center position. Accordingly, the target mark Tg is displayed at a position corresponding to the scanning center position when a fundus portion substantially the same as that of the past tomographic image is measured. The positional deviation amount $\Delta d1$ is continually detected by the control unit 70, and a display position of the target mark Tg is changed according to the detected positional deviation amount $\Delta d1$. An initial position of the scanning center indication SC corresponds to the past scanning center coordinates before correction, and therefore, when the detected positional deviation amount $\Delta d1$ is approximately 0, the scanning center indication SC and the target mark Tg are displayed in coincidence. In addition, when the detected positional deviation amount $\Delta d1$ is greater than 0, the relative distance between the scanning center indication SC and the target mark Tg is changed according to the positional deviation amount. In the present preferred embodiment of the present invention, a cross mark J extending vertically and laterally having the target mark Tg at the center is displayed, which allows the examiner to visually observe the display position of the target mark Tg.

Display of Guide Mark

The control unit 70 detects a positional deviation direction and a positional deviation amount $\Delta d2$ of the current scanning center position (corresponding to the scanning center indication SC) from the scanning target position (corresponding to the target mark Tg), and displays information on deviation of the current scanning position from the scanning target position based on a result of the detection.

Figure 5A:
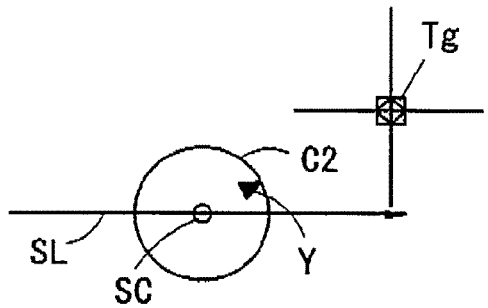
FIGS. 5A to 5C are views showing an example of displaying information on a positional deviation of a current scanning position from a scanning target position.
Figure 5B:
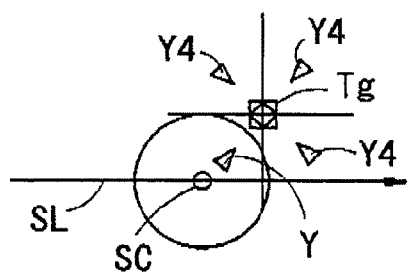

For example, a guide mark Y indicating the moving direction when adjusting the scanning center position is displayed (in the present preferred embodiment of the present invention, an arrow is displayed). The guiding direction (a direction indicated by the arrow) of the guide mark Y is changed based on the deviation direction of the current scanning center position from the scanning target position. Accordingly, the deviation direction of the scanning center indication SC from the target mark Tg is indicated. In the case of FIG. 5A, an upper right direction is specified by the arrow of the guide mark Y, which shows that an adjustment target is positioned upper right of the current scanning center position of the measurement light.

The display state (operation, color of the display) of the guide mark Y is changed based on the positional deviation amount $\Delta d2$. The drawing color of the past front image K is changed according to the positional deviation amount $\Delta d2$.

When $\Delta d2 > D1$

When the positional deviation amount $\Delta d2$ is greater than a first allowable range $\Delta 1$ ($\Delta d2 > D1$), the control unit 70 controls the display direction of the guide mark Y to indicate the deviation direction of the scanning center indication SC from the target mark Tg (see FIG. 5A). In addition, the control unit 70 makes the guide mark Y have a first color (e.g., red) and makes the past front image K have a first color (e.g., semi-transparent red). Thus, the examiner is informed that the positional deviation is great (the adjustment of the current scanning position is incomplete). In this case, the guide mark Y and the past front image K are made to have the same color.

When $\Delta d2 \leq D1$

When the positional deviation amount $\Delta d2$ is equal to or smaller than the first allowable range D1 ($\Delta d2 \leq D1$), the control unit 70 controls the display direction of the guide mark Y as described above and additionally displays four marks Y4 in the shape of an arrow having the target mark Tg at their center. In addition, the control unit 70 makes the guide mark Y have a second color (e.g., yellow) and makes the past front image K have a second color (e.g., semi-transparent yellow) (see 58). Thus, the examiner is informed that the positional deviation is small (the adjustment of the current scanning position is incomplete while the scanning center position is close to the scanning target Tg). In this case, one of the marks Y4 which is displayed between the target mark Tg and the scanning center indication SC doubles as the guide mark Y.

When $\Delta d2 \leq D2$

Figure 5C:
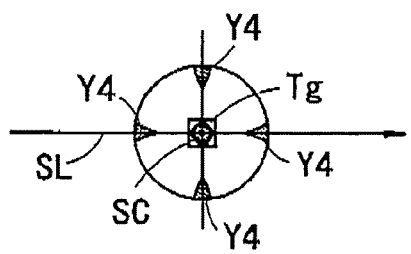

When the positional deviation amount $\Delta d2$ is equal to or smaller than a second allowable range D2 ($\Delta d2 \leq D2$), the control unit 70 fills in the marks Y4 (see FIG. 5C). Here, the control unit 70 makes the marks Y4 (the guide mark Y) have a third color (e.g., green). In addition, the control unit 70 makes the past front image K have a third color (e.g., semi-transparent green). It should be noted that the second allowable range D2 is smaller than the first allowable range D1. Thus, the examiner is informed that the positional deviation is resolved (the adjustment of the current scanning position is complete). In other words, the control unit 70 determines whether the continually detected positional deviation amount $\Delta d2$ satisfies the second allowable range D2 or not and displays a result of the determination on the monitor 75. Whether the adjustment of the current scanning position is complete or not is determined by this determination processing.

In the above-described display control, transmittance of the past front image K (the semi-transparent image) may be changed in accordance with the positional deviation amount $\Delta d2$. For example, the control unit 70 makes transmittance of the past front image K higher (lighten the color) as the positional deviation amount $\Delta d2$ is greater, and makes transmittance of the past front image K lower (darken the color) as the positional deviation amount $\Delta d2$ is smaller.

Display of Indicators G1 and G2

The control unit 70 detects the positional deviation amount $\Delta d1$ while dividing into a vertical positional deviation amount and a lateral positional deviation amount and controls display of indicators G1 and G2. In the lower portion of the two-dimensional image observation screen, the indicator G1 indicating the lateral positional deviation is displayed. The indicator G1 shows an increase or decrease based on the lateral positional deviation amount from the past front image K. In the right portion of the two-dimensional image observation screen, the indicator G2 indicating the vertical positional deviation amount is displayed. The indicator G2 shows an increase or decrease based on the vertical positional deviation amount from the past front image K. Colors of the indicators G1 and G2 are changed based on the positional deviation amount $\Delta d2$. In the present preferred embodiment of the present invention, the colors of the indicators G1 and G2 are changed in synchronization with the change of the color of the guide mark Y (the past front image K).

Adjustment of Measurement Position

Next, a description of setting a measurement position on the monitor 75 by the examiner is provided. When photographing is to be performed at the same position as the past testing, the examiner performs operation so that the given scanning target position and the current scanning center position coincide with each other.

When a given fixation target position adjusting unit (e.g., a mouse) is operated by the examiner, the fixation direction of the eye E is changed, and accordingly, the obtainment position of the front image is changed. Thus, the current front image Gf is moved on the two-dimensional image observation screen. At the same time, the positional deviation amount between the past front image K and the current front image Gf is changed, and accordingly, the target mark Tg is moved relative to the scanning center indication SC. The examiner adjusts the fixation position so that the scanning center indication SC and the target mark Tg coincide with each other.

When a given adjusting unit (e.g., a mouse) is operated by the examiner, the control unit 70 moves the scan lines SL relative to the target mark Tg. To be specific, the examiner moves the scan lines SL so that the scanning center indication SC and the target mark Tg coincide with each other.

When the positional relation between the scanning center indication SC and the target mark Tg is adjusted and an indication that the adjustment of the current scanning position is complete is displayed (see FIG. 5C), the examiner presses a photographing starting switch 74b. In this case, the current scanning center position reaches a scanning center target. The scanning center target is a position corresponding to the scanning center position when the fundus portion substantially the same as that of the past tomographic image is measured. Thus, when the scanning center position is positioned at the scanning center target, the current scanning position with the measurement light is set at the fundus portion substantially the same as that of the past tomographic image.

When a trigger signal for starting photographing (permitting photographing) is outputted from the photographing starting switch 74b, the control unit 70 obtains the tomographic image by operating the scanning unit 23 based on the set scanning position information and stores the obtained tomographic image as a still image in the memory 72. The obtained tomographic image is displayed parallel to the past tomographic image and follow up is performed.

Owing to the configuration described above, the image obtainment is easily performed at the same position as that of the image obtainment of the past tomographic image, and the testing can be efficiently performed.

Modified Example in Follow Up Mode

In the description provided above, the operation signal which is generated from the photographing starting switch by the examiner when the indication that the adjustment of the current scanning position is complete is displayed on the monitor 75 (i.e., when the scanning center position reaches the scanning center target) is taken as the trigger for starting photographing. However, the present invention is not limited thereto. For example, the control unit 70 may automatically generate a trigger signal for starting photographing (capturing images) when the control unit 70 determines that the continually detected positional deviation amount $\Delta d2$ is in the second allowable range D2. When the trigger signal is generated, the control unit 70 obtains the tomographic image by operating the scanning unit 23 based on the set scanning position information and stores the obtained tomographic image in the memory 72 in the same manner as described above. Because the present preferred embodiment of the present invention has a configuration that the tomographic images are obtained one by one as a moving image, one of the tomographic images obtained when the trigger signal is generated may be stored as a still image in the memory 72. The present invention is not limited to the method described above and may be configured such that the determination processing is performed on each of the tomographic images obtained one by one, the tomographic images and results of the determination are once stored in the memory 72, and one of the tomographic images obtained with the adjustment of the current scanning position being complete is extracted based on the determination result.

The description provided above states that the current scanning position with the measurement light is set to be the same as the obtainment position of the past tomographic image by manual operation of the examiner. However, the present invention is not limited thereto and may be applied to such a configuration that the scanning unit 23 is driven and controlled by the control unit 70 so that the positional deviation amount $\Delta d2$ is in the second allowable range D2. However, in consideration of the current performance of the control unit 70 and the speed of response of the scanning unit 23, a long time is required for the process from the detection of the positional deviation amount $\Delta d2$ to the completion of the driving of the scanning unit 23 (the completion of the movement to the given scanning target position). Thus, even if measurement is performed at the given scanning target position after the completion of the driving of the scanning unit 23, measurement could be performed at an unintended position if the eye E moves during the above-described process.

In contrast, the manual operation described above allows for smooth control even with the current configuration. To be specific, the determination as to whether the positional deviation amount $\Delta d2$ is in the second allowable range D2 is continually performed, and a result of the determination is displayed on the monitor 75 in real time. Thus, the examiner is allowed to perform accurate measurement by pressing the photographing starting switch while visually observing the determination result.

In the case of automatically changing the current scanning position, the control unit 70 detects the positional deviation amount $\Delta d2$ again after the completion of the driving of the scanning unit 23 based on the positional deviation amount $\Delta d2$ and determines whether the positional deviation amount $\Delta d2$ is in the second allowable range D2 or not. When the control unit 70 determines that the positional deviation amount $\Delta d2$ is in the second allowable range D2, the control unit 70 automatically generates a trigger signal for starting photographing (capturing images). In addition, when the control unit 70 determines that the positional deviation amount $\Delta d2$ is out of the second allowable range D2, the control unit 70 controls the driving of the scanning unit 23 to change the current scanning position again. Accordingly, the possibility of measuring an unintended position is minimized.

The description provided above states that the light scanning unit is used as a fundus observation optical system arranged to obtain a front fundus image. However, the present invention is not limited thereto and may have a configuration of using an optical system arranged to illuminate the whole fundus at a time and an image-pickup optical system arranged to pick up a fundus image by using a two-dimensional photodetector (a so-called fundus camera type).

In addition, the description provided above takes the obtainment of the fundus tomographic image as an example. However, the present invention is not limited thereto and may be applied to any ophthalmic photographing apparatus arranged to obtain a tomographic image of a given portion of the eye by using an optical interference optical system based on the principle of OCT (e.g., an anterior-segment tomographic image).

Obtainment of Average Image

Figure 6:
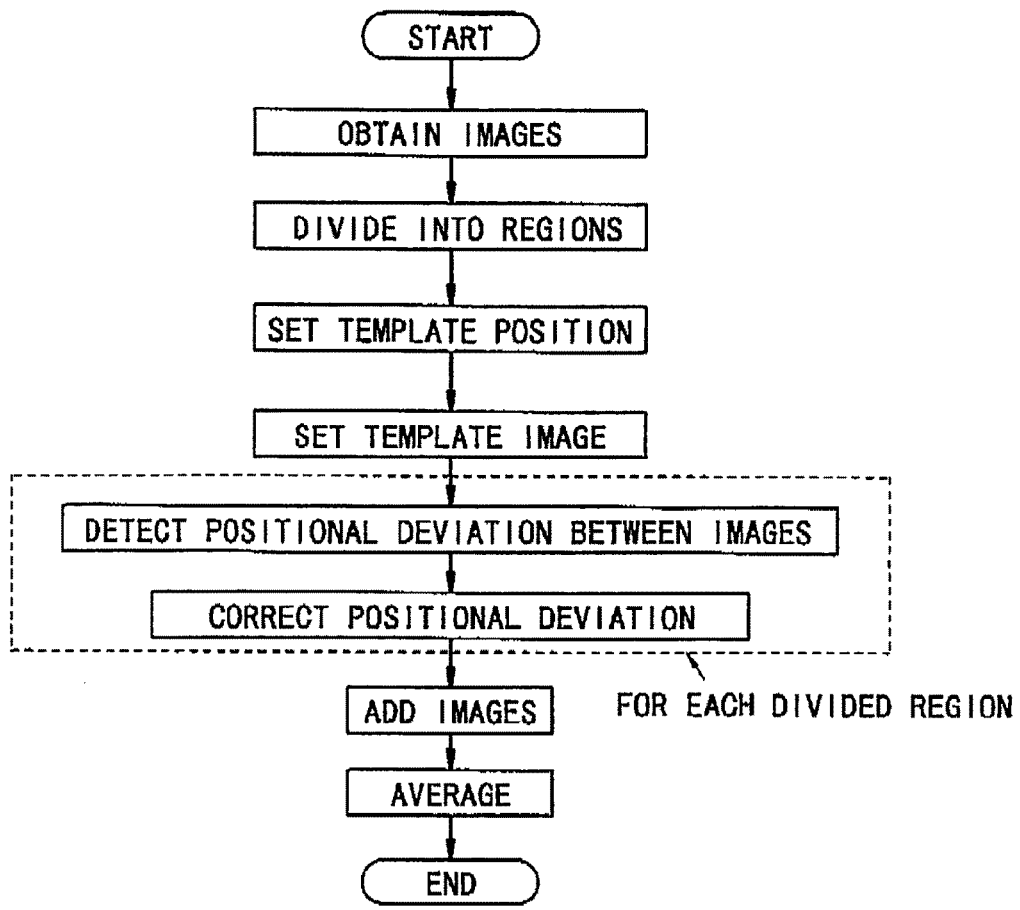
FIG. 6 is a flow chart representing a process of obtaining a plurality of tomographic images by B-scan and making an average image.

Next, a description of a process of obtaining a plurality of tomographic images by the B-scan and making an average image is provided (see the flow chart in FIG. 6). According to the present preferred embodiment of the present invention, in order to obtain one tomographic image with less noise components (the B-scan image), the scanning with the measurement light is performed a plurality of times in a given scanning region to obtain a plurality of tomographic images, and the obtained tomographic images are added and averaged by the control unit 70. The control unit 70 divides each of the tomographic images into a plurality of regions relative to the scanning direction with the measurement light, and obtains positional deviation information by detecting a positional deviation between the tomographic images for each of the divided regions. Then, based on the obtained positional deviation information, the control unit 70 corrects the positional deviation between the tomographic images for each of the divided regions. The control unit 70 adds the corrected tomographic images and averages them.

Obtainment of a Plurality of Tomographic Images

First, the control unit 70 performs the scanning with the measurement light a plurality of times in the given scanning region by using the scanning unit 23, obtains a plurality of tomographic images (n pieces (n>2)) in one scanning region, and stores the tomographic images in the memory 72.

Image Division Relative to Scanning Direction

Figure 7:
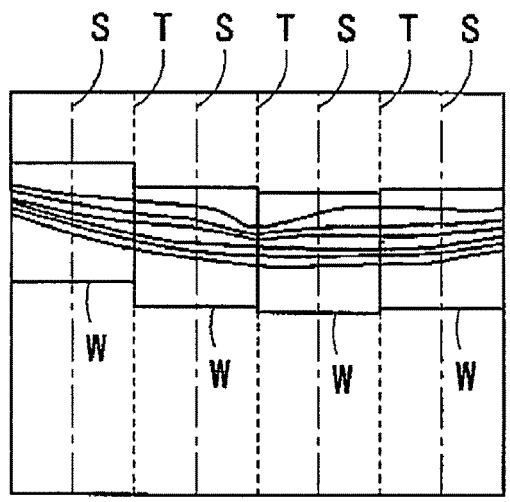
FIG. 7 is a view showing an example of dividing each of the tomographic images into a plurality of regions.

Next, the control unit 70 sections each of the tomographic images stored in the memory 72 at a given width (see the broken lines T shown in FIG. 7) to divide the tomographic image into a plurality of regions. In this case, the tomographic image is divided into the plurality of regions relative to the scanning direction with the measurement light by the scanning unit 23 (e.g. the X-direction). Although the tomographic image is divided into four regions according to the present preferred embodiment of the present invention, the number of division may be arbitrarily set according to resolution of the tomographic image, a period of time required for obtaining the tomographic image, an expected positional deviation amount, and other factors.

Setting Template Image

The control unit 70 specifies a position which meets preset luminance conditions such as a position with a highest luminance based on the A-scan signal at a center position of each of the divided regions (see dashed dotted lines S in FIG. 7), and sets the specified position as a template position (a reference position). Then, the control unit 70 takes an image within an arbitrary region having the template position at the center (e.g., a rectangular region) as a template image (see rectangles W in FIG. 7). Thus, the template image used in the positional deviation detection is set in each of the divided regions.

The method described above is used for extracting a tomographic image corresponding to a retinal portion of the eye as the template image for the positional deviation detection. Setting the template position may be performed such that a position with a luminance value that exceeds a given threshold value corresponding to a luminance value in a retinal pigment epithelium portion (in the retinal pigment epithelium portion, a relatively high luminance value is obtained) is specified, and the specified position is set as the template position.

The control unit 70 selects one of the n pieces of tomographic images (e.g., the 2nd one) as a base image (a reference image) and retrieves the template images in the divided regions of the base image.

Detection of Positional Deviation Between Tomographic Images

Next, the control unit 70 selects one of the tomographic images and adds the selected tomographic image on the base image. The control unit 70 repeats this operation and finally adds at least three or more tomographic images.

To be specific, the control unit 70 selects one of the n pieces of tomographic images and retrieves the template images in the divided regions of the selected tomographic image. Then, the control unit 70 compares the template images of the base image and the template images of the selected image for each of the divided regions, and detects the positional deviation direction and the positional deviation amount of the selected image from the based image for each of the divided regions. In this case, the control unit 70 continually calculates a correlation value while displacing on a pixel basis the template image of the selected image with respect to the template image of the base image. Then, the control unit 70 calculates a pixel displacement amount of the template image (the number of pixels by which the template image is displaced) when the correlation value becomes greatest as the positional deviation amount.

Correction of Positional Deviation, Addition, and Average

The control unit 70 displaces the template images of the selected image for each of the divided regions with respect to the base image by the positional deviation amount detected in each of the divided regions in order that the positional deviation is corrected. After the positional deviation correction, the control unit 70 adds the pixel value of the template image of the base image and the pixel value of the template image of the selected image for each of the divided regions.

As described above, the control unit 70 repeats the positional deviation detection and the positional deviation correction within the whole tomographic image, and calculates the sum of the pixel values. Then, the control unit 70 divides the sum of the pixel values by the number of tomographic images added, whereby an average image in obtained. In this case, the tomographic image having a positional deviation amount out of the given allowable range may be eliminated from the object of the addition. The description provided above states that the image addition is successively performed on the divided regions on a tomographic-image basis. However, the image addition may be performed on the tomographic images on a divided-region basis.

In the configuration described above, the positional deviation correction is performed on each of the divided regions which are divided relative to the scanning direction with the measurement light. Therefore, even if the eye finely moves during the scanning with the measurement light, the deviation between the added tomographic images is properly corrected, and a clear tomographic image is obtained.

Modified Example of Obtainment of Average Image

The present invention is not limited to the configuration described above and may be applied to other methods that allow for the detection of the positional deviation between the tomographic images for each of the divided regions and the correction of the positional deviation between the tomographic images. For example, a positional deviation between the tomographic images temporally adjacent to each other may be successively corrected.

In addition, the present invention is not limited to the configuration described above and may be applied to any ophthalmic photographing apparatus arranged to obtain a tomographic image of a given portion of the eye (e.g., an anterior-segment tomographic image) by using a light interference optical system based on the principle of OCT.

In addition, the description provided above describes the image addition method when obtaining the tomographic image of the eye by using the interference optical system. However, the present invention may be applied to an image addition method of obtaining a plurality of front images by using a confocal optical system (e.g., the SLO optical system 300) having a light source arranged to emit light with high intensity and high directivity, a light scanning unit arranged to scan a given portion of the eye with measurement light, a photodetector arranged to photo-receive reflection light formed by the measurement light through a confocal opening disposed at a position substantially conjugate with the given portion of the eye and arranged to obtain a front image of the given portion of the eye. For example, when a plurality of SLO fundus images are obtained by the SLO optical system 300, each of the SLO fundus images is divided into a plurality of regions with respect to the auxiliary scanning direction with the measurement light (the vertical direction). A positional deviation between the SLO fundus images is detected for each of the divided regions, the positional deviation between the SLO fundus images is corrected for each of the divided regions based on the detected positional deviation, and the image addition is performed.

In addition, the present invention is not limited to the configuration described above and may be applied to any photographing optical system having a light scanning unit arranged to scan a given portion of the eye with light emitted from a measurement light source and a photodetector arranged to photo-receive reflection light formed by the measurement light and arranged to obtain a tomographic image or a front image of the eye.

Evaluation of Three-Dimensional Image Obtainment Of Three-Dimensional Image

Figure 8:
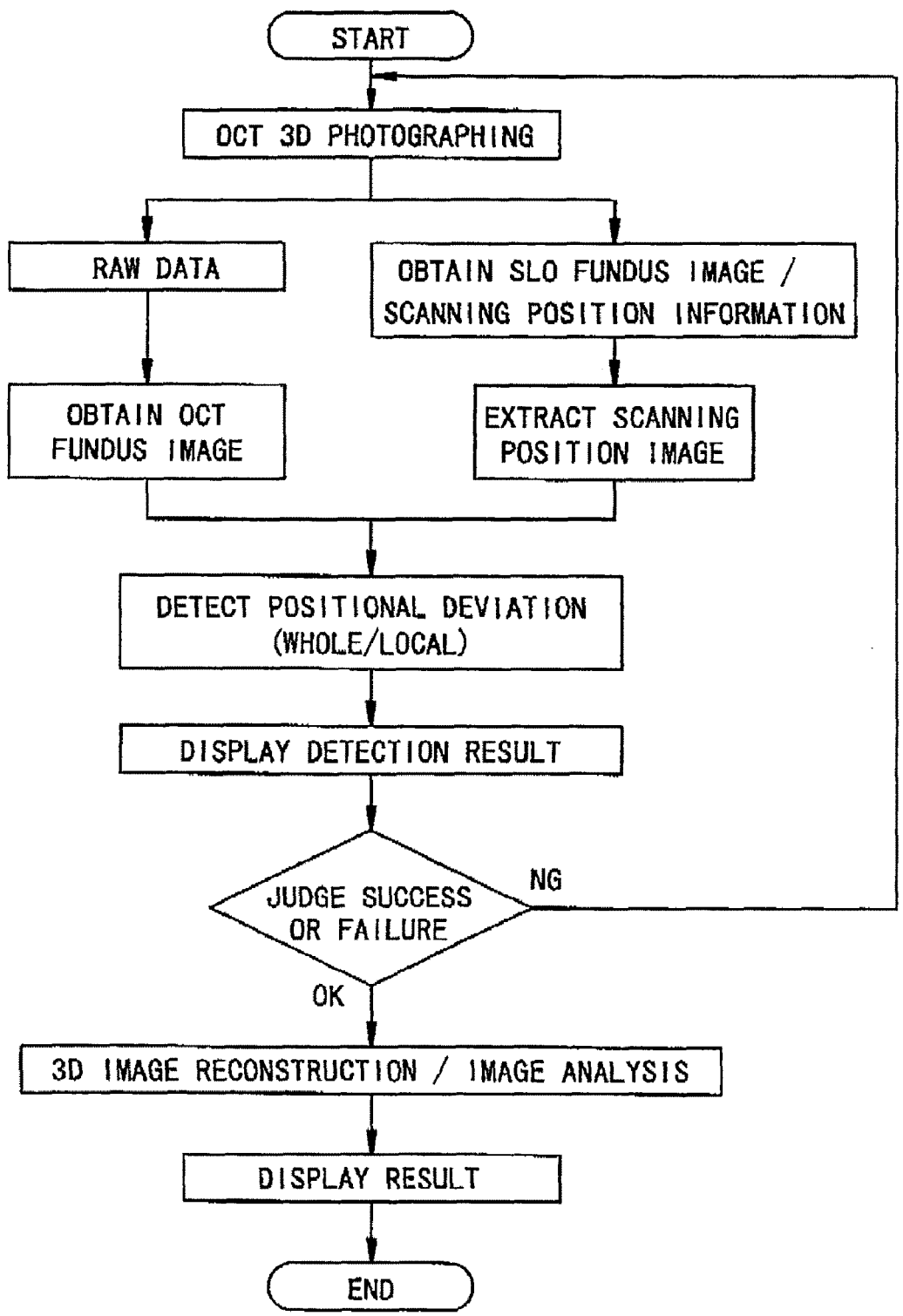
FIG. 8 is a flow chart representing a process of obtaining a three-dimensional image of a fundus by using an OCT optical system.

Next, a description of obtaining a three-dimensional image of the fundus by using the OCT optical system 200 is provided (see the flow chart in FIG. 8). With the use of a given scanning position adjusting unit and a given fixation target position adjusting unit, the examiner sets a region on the fundus where a three-dimensional image is to be obtained by operating a setting switch not shown, and presses the photographing starting switch. Accordingly, the three-dimensional image obtainment by the OCT optical system 200 is started. The three-dimensional image is obtained based on the photo-receiving signal outputted from the photodetector 83 when the fundus is scanned two-dimensionally (in the X- and Y-directions) with the measurement light by the driving of the scanning unit 23. In the present preferred embodiment of the present invention, the OCT light source 27 is turned on and the SLO light source 61a is turned off during the three-dimensional image obtainment.

Obtainment of OCT Front Fundus Image

Upon completion of the scanning with the measurement light for the three-dimensional image obtainment, the control unit 70 extracts interference signals from primary data (raw data) of the photo-receiving signals outputted from the photodetector 83 before performing the Fourier analysis (removing stationary reference light components), and adds the interference signals for each A-scan and places them parallel to each other. Thus, a front fundus image by the OCT optical system 200 by the three-dimensional image obtainment (hereinafter, referred to as an OCT fundus image) is obtained (see FIGS. 9A to 9C). A luminance level at a given position on the OCT fundus image corresponds to a cumulative total value of signal levels (luminance values) for each pixel of the interference signals extracted from the photo-receiving signals outputted from the photodetector 83 at the given scanning position.

The OCT fundus image described above is an image formed based on the photo-receiving signals before performing the Fourier analysis. Therefore, the time required for making the image (the Lime required for image processing) may be short. The obtainment of the OCT fundus image by the three-dimensional image obtainment is not limited to the method described above and may be performed by any method of obtaining the OCT fundus image based on the interference signals from the photodetector 83 during the three-dimensional image obtainment. For example, the OCT fundus image may be obtained as an accumulated image which is obtained by accumulating the three-dimensional image in the depth direction by performing the Fourier analysis (however, the time for the Fourier analysis is necessary). In addition, an image of a fundus surface portion in the three-dimensional image may be obtained as the OCT fundus image.

Obtainment of SLO Front Fundus Image

The control unit 70 obtains a front fundus image, which is obtained in the same fixation state as the OCT fundus image, as a reference image by using the SLO optical system 300 (hereinafter, referred to as an SLO fundus image) before or after the three-dimensional image obtainment, and stores the SLO fundus image in the memory 72. Then, the control unit 70 extracts an image of a portion corresponding to a region in which the three-dimensional image is obtained from the SLO fundus image based on the information on the scanning position with the measurement light for the three-dimensional image obtainment. The extracted SLO fundus image is used as a reference image for obtaining a positional deviation from the above-described OCT fundus image. The obtainment of the SLO fundus image to be used as the reference image is made substantially simultaneously with the three-dimensional image obtainment, and the SLO fundus image may be obtained during the three-dimensional image obtainment.

Detection of Positional Deviation (Whole/Local)

Upon completion of the obtainment of the OCT fundus image and the SLO fundus image, the control unit 70 compares the OCT fundus image and the reference image (the SLO fundus image) to detect the positional deviation of the OCT fundus image from the reference image by image processing, and displays a result of the detection and the OCT fundus image on the monitor 75. To be specific, the control unit 70 compares the OCT fundus image and the reference image to detect the whole positional deviation amount of the OCT fundus image from the reference image. In addition, the control unit 70 divides the whole OCT fundus image into a plurality of regions, and compares the OCT fundus image and the reference image in each of the divided regions to detect a local positional deviation amount of the OCT fundus image from the reference image.

Example of Obtainment of OCT Fundus Image

FIGS. 9A to 9C are views showing examples of the OCT fundus image obtained by the three-dimensional image obtainment. FIG. 9A is a view showing a favorable OCT fundus image with no fixation deviation and no blink during the three-dimensional image obtainment. On the other hand, when blink occurs during the three-dimensional image obtainment, the measurement light is repelled by an eyelid, and a portion of the OCT fundus image is omitted (see the portion K in FIG. 9B). When the fixation position deviates during the three-dimensional image obtainment, a different fundus portion is scanned with the measurement light, whereby the OCT fundus image includes a partial deviation (the deviation at the broken line D in FIG. 9C).

Considering that the time for obtaining the SLO fundus image is shorter than the time for obtaining the OCT fundus image, there is slight possibility that fixation deviation or blink occurs during the obtainment of the SLO fundus image. However, it is preferable to obtain a plurality of SLO fundus images and use a favorable SLO fundus image in the obtained SLO fundus images as the reference image by way of precaution.

Detection of Whole Positional Deviation

When detecting the whole positional deviation amount between the SLO fundus image and the OCT fundus image, the control unit 70 continually calculates a correlation value while displacing the whole OCT fundus image with respect to the whole SLO fundus image on a one-pixel basis, for example. Then, the control unit 70 calculates (detects) a pixel displacement amount (the number of pixels by which the whole OCT fundus image is displaced) when the correlation value becomes greatest as the positional deviation amount. Thus, a positional deviation amount of an actual obtainment position from the obtainment position set before the three-dimensional image obtainment is obtained.

Detection of Local Positional Deviation

When detecting the local (partial) positional deviation amount between the SLO fundus image and the OCT fundus image, the control unit 70 divides the OCT fundus image into a plurality of regions as shown in FIG. 10A and calculates a positional deviation amount between the OCT fundus image in each of the divided regions and the SLO fundus image, for example. In this case, the control unit 70 continually calculates a correlation value of the OCT fundus image with respect to the SLO fundus image for each of the divided regions. Then, the control unit 70 calculates a pixel displacement amount (the number of pixels by which the OCT fundus image is displaced) when the correlation value becomes greatest as the positional deviation amount in each of the divided regions. Thus, the local positional deviation amount of the obtainment position by the movement of the eye during the three-dimensional image obtainment and the occurrence of blink are obtained. When blink occurs, the positional deviation amount shows an abnormal value. In the obtainment of the local positional deviation amount, the SLO fundus image may be divided into a plurality of regions in the same manner as the OCT fundus image, and the positional deviation of the OCT fundus image from the SLO fundus image is obtained for each of the divided regions.

According to the present preferred embodiment of the present invention, the control unit 70 divides the OCT fundus image into a plurality of regions so that the number of pixels in the vertical direction and the number of pixels in the lateral direction in each of the divided regions are equal as shown in FIG. 10A. For example, when the number of pixels in the whole OCT fundus image is 256 by 256, the OCT fundus image is divided into 16 regions of four columns and four rows, each region having 64 by 64 pixels (see the thin lines in the image in FIG. 10A). Thus, local rotational movement of the eye can be supported. The present invention is not limited to the method described above, and the OCT fundus image may be divided into a plurality of regions only in the vertical direction (the auxiliary scanning direction with the measurement light). In addition, the size of each the divided regions is required to provide such a region that the positional deviation can be detected by comparison with the reference image.

Display of Detection Result

When the positional deviation of the OCT fundus image from the reference image (the SLO fundus image) is detected as described above, the control unit 70 displays a result of the detection on the monitor 75. The control unit 70 displays the whole positional deviation amount and the local positional deviation amount detected in each region on the monitor 75.

As an output format, the positional deviation may be displayed by using a given unit (e.g., by using the unit pixel) (see FIG. 10B). As another output format, whether the detected positional deviation amount is in a given allowable range or not is determined by the control unit 70, and a result of the determination is outputted (e.g., giving an indication such as "POSITIONAL DEVIATION OK" and "POSITIONAL DEVIATION ERROR", and changing the drawing color according to the determination result). In addition, the positional deviation may be indicated by numbers indicating the positional deviation stepwise, may be ranked by alphabets, or may be displayed as a confidence coefficient indicating the reliability of the three-dimensional image. When making a display about the local positional deviation, the display is preferably outputted while associating the divided regions and the positional deviation amounts.

Three-Dimensional Image Reconstruction/Image Analyses

The examiner judges the success or failure of the three-dimensional image obtainment while observing the determination result and the OCT fundus image on the monitor 75 (the SLO fundus image may also be displayed). If the whole positional deviation amount or the local positional deviation amount is smaller than an allowable value, the examiner judges that the three-dimensional image obtainment is successful. When the three-dimensional image obtainment is judged to be successful and the given switch operation is made, the control unit 70 successively performs the Fourier analysis, reconstruction of a three-dimensional image, image analysis (e.g., detection of boundary positions of membranes, measurement of thicknesses of the membranes). Then, the control unit 70 displays graphics of the three-dimensional image and a result of the image analysis on the monitor 75.

If the whole positional deviation amount or the local positional deviation amount is greater than the allowable value, the examiner performs the three-dimensional image obtainment again. If it is judged that the three-dimensional image obtainment is to be performed again and a given switch operation is made, the control unit 70 performs the three-dimensional image obtainment again.

By detecting the deviation of the obtainment position during the three-dimensional image obtainment and displaying a result of the detection on the monitor 75 as described above, it is easily possible for the examiner to know the deviation of the actual obtainment position from the set obtainment position, the deviation of the fixation position and the alignment position during the three-dimensional image obtainment, the occurrence of blink, and others. In addition, the method described above allows for the judgment of the success or failure of the three-dimensional image obtainment before performing the Fourier analysis, the reconstruction of the graphics, and the image analysis, a waiting time for the re-obtainment when the three-dimensional image obtainment fails can be shortened.

Modified Example of Three-Dimensional Image Evaluation

The description provided above states that the examiner judges the success or failure of the three-dimensional image obtainment. However, the present invention is not limited thereto and may be applied to a configuration that the success or failure of the three-dimensional image obtainment is determined by the control unit 70 and re-obtainment is automatically performed based on a result of the determination. In this case, the control unit 70 determines whether at least one of the whole positional deviation amount and the local positional deviation amount is in the given allowable ranges or, not, and if it is determined that one of the positional deviation amounts is out of the given allowable range, re-obtainment of the three-dimensional image is automatically performed.

The description provided above states that the front fundus image for observation obtained substantially simultaneously with the three-dimensional image obtainment is used as the reference image. However, a front fundus image for observation obtained substantially simultaneously with the three-dimensional image obtainment in times past in the same fundus portion. Accordingly, it becomes possible to judge whether the three-dimensional image obtainment was successfully performed in the same fundus portion as in the past testing.

In addition, the description provided above states that the light scanning unit is provided as a fundus observation optical system arranged to obtain the front fundus image for observation. However, the present invention is not limited thereto and may be applied to a configuration of using an optical system arranged to illuminate the whole fundus at once and an image-pickup optical system arranged to pick up an image of the fundus by using a two-dimensional photodetector (a so-called fundus camera type).

The description provided above describes the method of judging the success or failure of the three-dimensional image obtainment on the fundus. However, the present invention is not limited thereto and may be applied to any ophthalmic photographing apparatus arranged to obtain a tomographic image of a given portion of the eye (e.g., an anterior-segment tomographic image) by using an optical interference optical system based on the principle of OCT.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic photographing apparatus arranged to obtain an image of an examinee's eye, the apparatus comprising:
    a photographing unit comprising
        a projection optical system comprising a light source and a scanner arranged to change a reflection direction of light, and arranged to scan a given portion of the eye in X- and Y-directions with at least a part of the light emitted from the light source defining measurement light, and
        a photo-receiving optical system comprising one or more photodetectors and arranged to make the measurement light reflected from the given portion of the eye enter the one or more photodetectors;
    a photographing control unit arranged to control operation of the photographing unit to scan the given portion a plurality of times in a given scanning region and obtain a plurality of pieces of image information based on a signal from the one or more photodetectors; and
    an image information processing unit arranged to
        (a) divide the scanning region in the X- and Y-directions of each of the plurality of pieces of image information into a plurality of regions and obtain information on a positional deviation between the plurality of pieces of image information for each of the divided regions,
        (b) obtain image information for each of the divided regions, in each of which the positional deviation has been corrected, with reference to one of the plurality of pieces of image information based on the obtained positional deviation information, and
        (c) add and average the plurality of pieces of image information for each of their corresponding divided regions to obtain one piece of image information.

2. The ophthalmic photographing apparatus according to claim 1, wherein the photographing unit further comprises an interference optical system arranged to divide the light from the light source into measurement light and reference light, guide the reference light to a reference optical system, and combine the measurement light reflected from the given portion and the reference light into interference light by using a light combining member, and makes the interference light enter the one or more photodetectors.

3. The ophthalmic photographing apparatus according to claim 1, wherein:
    the photographing unit further comprises a confocal optical system comprising
        a light source arranged to emit light with high intensity and high directivity, and
        a confocal opening disposed at a position substantially conjugate with the given portion of the eye.

4. The ophthalmic photographing apparatus according to claim 1, wherein:
    the photographing unit further comprises
        a confocal optical system comprising a light source arranged to emit light with high intensity and high directivity and a confocal opening disposed at a position substantially conjugate with the given portion of the eye; and
    the image information processing unit is arranged to divide the scanning region into the plurality of regions with reference to an auxiliary scanning direction with respect to a main scanning direction.

5. An ophthalmic photographing apparatus arranged to obtain an image of an examinee's eye, the apparatus comprising:
    a photographing unit comprising
        an interference optical system comprising a light source and arranged to divide light emitted from the light source into measurement light and reference light, guide the reference light to a reference optical system, guide the measurement light to a projection optical system arranged to scan a given portion of the eye in X- and Y-directions with the measurement light by using a scanner, and combine the measurement light reflected from the given portion and the reference light into interference light by using a light combining member, and arranged to make the interference light enter one or more photodetectors;
    a photographing control unit arranged to control operation of the photographing unit, scan a plurality of times the given portion in a given scanning region, and obtain a plurality of pieces of image information by obtaining a signal from the one or more photodetectors; and
    an image information processing unit arranged to
        (a) divide the scanning region in the X- and Y-directions of each of the pieces of image information into a plurality of regions and obtain information on a positional deviation between the pieces of image information for each of the divided regions,
        (b) obtain image information for each of the divided regions, in each of which the positional deviation has been corrected, with reference to one of the plurality of piece of image information based on the obtained positional deviation information, and
        (c) add and average the plurality of pieces of image information for each of their corresponding divided regions to obtain one piece of image information.

6. The ophthalmic photographing apparatus according to claim 5, wherein:
    the interference optical system comprises an optical system arranged to disperse the interference light into frequency components and make the interference light enter an array of the one or more photodetectors; and
    the image information processing unit is arranged to specify a position which satisfies a given luminance condition based on image information in a depth direction at a position in the X- and Y-directions in each of the divided regions, obtain a template image for obtaining a positional deviation based on the specified position, and obtain information on a positional deviation of other images by comparing images other than the template image with the template image.

7. The ophthalmic photographing apparatus according to claim 6, wherein the position which satisfies the given luminance condition comprises a center position in each of the divided regions.

8. The ophthalmic photographing apparatus according to claim 6, wherein the position which satisfies the given luminance condition comprises a position at which luminance becomes greatest.

9. The ophthalmic photographing apparatus according to claim 6, wherein the position which satisfies the given luminance condition comprises a position of a retinal pigment epithelium portion.

10. The ophthalmic photographing apparatus according to claim 5, wherein the image information comprises a tomographic image of a fundus.

* * * * *